United States Patent
Lafontaine et al.

(10) Patent No.: US 8,398,677 B2
(45) Date of Patent: Mar. 19, 2013

(54) CLOSURE DEVICE WITH TEXTURED SURFACE

(75) Inventors: Daniel M. Lafontaine, Plymouth, MN (US); Mark T. Ungs, Minnetonka, MN (US); William J. Drasler, Minnetonka, MN (US); Sheng-Ping (Samuel) Zhong, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 12/790,554

(22) Filed: May 28, 2010

(65) Prior Publication Data

US 2010/0234884 A1  Sep. 16, 2010

Related U.S. Application Data

(63) Continuation of application No. 10/325,710, filed on Dec. 20, 2002, now abandoned.

(51) Int. Cl.
*A61B 17/08* (2006.01)
(52) U.S. Cl. ..................... 606/213
(58) Field of Classification Search .............. 606/213, 606/214, 215, 216, 229, 232
See application file for complete search history.

(56) References Cited

U.S. PATENT DOCUMENTS

| | | |
|---|---|---|
| 3,438,374 A | 4/1969 | Falb et al. |
| 4,002,173 A | 1/1977 | Manning et al. |
| 4,068,655 A | 1/1978 | LeRoy |
| 4,140,537 A | 2/1979 | Luck et al. |
| 4,292,972 A | 10/1981 | Pawelchak et al. |
| 4,365,621 A | 12/1982 | Brundin |
| 4,372,314 A | 2/1983 | Wall |
| 4,390,519 A | 6/1983 | Sawyer |
| 4,404,970 A | 9/1983 | Sawyer |
| 4,405,324 A | 9/1983 | Cruz, Jr. |
| 4,424,208 A | 1/1984 | Wallace et al. |
| 4,509,504 A | 4/1985 | Brundin |
| 4,515,637 A | 5/1985 | Cioca |
| 4,543,410 A | 9/1985 | Cruz, Jr. |
| 4,582,640 A | 4/1986 | Smestad et al. |
| RE32,208 E | 7/1986 | Mattei et al. |
| 4,597,960 A | 7/1986 | Cohen |
| 4,703,108 A | 10/1987 | Silver et al. |
| 4,744,364 A | 5/1988 | Kensey |
| 4,749,689 A | 6/1988 | Miyata et al. |
| 4,852,568 A | 8/1989 | Kensey |
| 4,890,612 A | 1/1990 | Kensey |
| 4,979,947 A | 12/1990 | Berman |
| 5,021,059 A | 6/1991 | Kensey et al. |
| 5,061,274 A | 10/1991 | Kensey |

(Continued)

FOREIGN PATENT DOCUMENTS

| | | |
|---|---|---|
| EP | 0044624 A1 | 6/1981 |
| EP | 0044624 B1 | 10/1984 |

(Continued)

*Primary Examiner* — Tuan V Nguyen
(74) *Attorney, Agent, or Firm* — Seager, Tufte & Wickhem LLC (57) ABSTRACT

A closure device closes an opening in a body cavity. The closure device includes a plurality of fibrous tissue engaging members coupled to a proximally extending elongate member, a closure sheath sized to receive the elongate member and slidable over the elongate member to move the fibrous tissue engaging members from an expanded position to a collapsed position, a delivery sheath sized to receive the closure sheath and having a distal end sized to engage the fibrous tissue engaging members in the expanded position, and a closure member having an aperture sized to receive the closure sheath.

11 Claims, 9 Drawing Sheets

U.S. PATENT DOCUMENTS

| | | | |
|---|---|---|---|
| 5,100,429 A | 3/1992 | Sinofsky et al. | |
| 5,108,421 A | 4/1992 | Fowler | |
| 5,192,300 A | 3/1993 | Fowler | |
| 5,192,302 A | 3/1993 | Kensey et al. | |
| 5,254,105 A | 10/1993 | Haaga | |
| 5,290,310 A | 3/1994 | Makower et al. | |
| 5,292,309 A | 3/1994 | Van Tassel et al. | |
| 5,292,332 A | 3/1994 | Lee | |
| 5,310,407 A | 5/1994 | Casale | |
| 5,320,639 A | 6/1994 | Rudnick | |
| 5,324,306 A | 6/1994 | Makower et al. | |
| 5,330,445 A | 7/1994 | Haaga | |
| 5,334,216 A * | 8/1994 | Vidal et al. | 606/213 |
| 5,376,376 A | 12/1994 | Li | |
| 5,383,891 A | 1/1995 | Walker | |
| 5,383,897 A | 1/1995 | Wholey | |
| RE34,866 E | 2/1995 | Kensey et al. | |
| 5,391,183 A | 2/1995 | Janzen et al. | |
| 5,431,639 A | 7/1995 | Shaw | |
| 5,449,375 A | 9/1995 | Vidal et al. | |
| 5,456,693 A | 10/1995 | Conston et al. | |
| 5,460,621 A | 10/1995 | Gertzman et al. | |
| 5,486,195 A | 1/1996 | Myers et al. | |
| 5,522,840 A | 6/1996 | Krajicek | |
| 5,540,715 A | 7/1996 | Katsaros et al. | |
| 5,545,180 A | 8/1996 | Le et al. | |
| 5,569,297 A | 10/1996 | Makower et al. | |
| 5,591,205 A | 1/1997 | Fowler | |
| 5,603,698 A | 2/1997 | Roberts et al. | |
| 5,624,669 A | 4/1997 | Leung et al. | |
| 5,643,318 A | 7/1997 | Tsukernik et al. | |
| 5,643,596 A | 7/1997 | Pruss et al. | |
| 5,645,849 A | 7/1997 | Pruss et al. | |
| 5,690,674 A | 11/1997 | Diaz | |
| 5,728,132 A | 3/1998 | Van Tassel et al. | |
| 5,782,860 A | 7/1998 | Epstein et al. | |
| 5,782,861 A | 7/1998 | Cragg et al. | |
| 5,823,198 A | 10/1998 | Jones et al. | |
| 5,868,762 A | 2/1999 | Cragg et al. | |
| 5,895,412 A | 4/1999 | Tucker | |
| 5,906,631 A | 5/1999 | Imran | |
| 5,964,782 A * | 10/1999 | Lafontaine et al. | 606/213 |
| RE36,370 E | 11/1999 | Li | |
| 5,984,950 A | 11/1999 | Cragg et al. | |
| 6,071,300 A | 6/2000 | Brenneman et al. | |
| 6,071,301 A | 6/2000 | Cragg et al. | |
| 6,086,607 A | 7/2000 | Cragg et al. | |
| 6,162,192 A | 12/2000 | Cragg et al. | |
| 6,162,240 A | 12/2000 | Cates et al. | |
| 6,183,496 B1 | 2/2001 | Urbanski | |
| 6,183,497 B1 | 2/2001 | Sing et al. | |
| 6,183,498 B1 | 2/2001 | Devore et al. | |
| 6,200,328 B1 | 3/2001 | Cragg et al. | |
| 6,267,761 B1 | 7/2001 | Ryan | |
| 6,270,464 B1 | 8/2001 | Fulton, III et al. | |
| 6,296,657 B1 | 10/2001 | Brucker | |
| 6,299,619 B1 | 10/2001 | Greene, Jr. et al. | |
| 6,315,753 B1 | 11/2001 | Cragg et al. | |
| 6,325,789 B1 | 12/2001 | Janzen et al. | |
| 6,350,274 B1 | 2/2002 | Li | |
| 6,440,151 B1 | 8/2002 | Cragg et al. | |
| 6,440,153 B2 | 8/2002 | Cragg et al. | |
| 6,447,534 B2 | 9/2002 | Cragg et al. | |
| 6,500,152 B1 | 12/2002 | Illi | |
| 6,500,190 B2 | 12/2002 | Greene, Jr. et al. | |
| 6,554,851 B1 | 4/2003 | Palasis et al. | |
| 6,623,509 B2 | 9/2003 | Ginn | |
| 6,663,655 B2 | 12/2003 | Ginn et al. | |
| 6,726,696 B1 | 4/2004 | Houser et al. | |
| 6,790,220 B2 | 9/2004 | Morris et al. | |
| 7,875,054 B2 * | 1/2011 | LaFontaine | 606/213 |
| 7,942,897 B2 * | 5/2011 | Lafontaine | 606/213 |
| 2002/0010150 A1 | 1/2002 | Cortese et al. | |
| 2002/0025921 A1 | 2/2002 | Petito et al. | |
| 2002/0077657 A1 | 6/2002 | Ginn et al. | |
| 2003/0013989 A1 | 1/2003 | Obermiller et al. | |

FOREIGN PATENT DOCUMENTS

| | | |
|---|---|---|
| EP | 0145970 A2 | 11/1984 |
| EP | 0467516 A1 | 5/1991 |
| EP | 1269951 A1 | 1/2003 |
| EP | 0891193 B1 | 8/2003 |
| JP | 55116736 A | 9/1980 |
| JP | 62004232 A | 1/1987 |
| JP | 63070507 A | 3/1988 |
| JP | 02182259 A | 7/1990 |
| JP | 05163157 A | 6/1993 |
| JP | 09294765 A | 11/1997 |
| JP | 2002143210 A | 5/2002 |
| RU | 2122867 C1 | 12/1998 |
| RU | 2135105 C1 | 8/1999 |
| RU | 2165741 C1 | 4/2001 |
| RU | 2178681 C2 | 1/2002 |
| RU | 2179859 C1 | 2/2002 |
| RU | 2180539 C2 | 3/2002 |
| RU | 2185858 C1 | 7/2002 |
| WO | 9325255 A2 | 12/1993 |
| WO | 9512371 A1 | 5/1995 |
| WO | 9640033 A1 | 12/1996 |
| WO | 9737694 A1 | 10/1997 |
| WO | 0019912 A1 | 4/2000 |
| WO | 0029484 A1 | 5/2000 |
| WO | 0156475 A1 | 8/2001 |
| WO | 0182937 A1 | 11/2001 |
| WO | 0197826 A2 | 12/2001 |
| WO | 0209591 A2 | 2/2002 |
| WO | 0209591 A3 | 2/2002 |
| WO | 02054998 A1 | 7/2002 |
| WO | 02072128 A1 | 9/2002 |
| WO | 02096302 A1 | 12/2002 |
| WO | 03002168 A1 | 1/2003 |

* cited by examiner

CLOSURE DEVICE WITH TEXTURED SURFACE

RELATED APPLICATIONS

This application is a continuation of U.S. patent application Ser. No. 10/325,710, filed Dec. 20, 2002, now abandoned, which is incorporated herein by reference.

BACKGROUND OF THE INVENTION

The present invention relates to closing openings in a vessel or other body cavity. More specifically, the present invention relates to a closure device that quickly closes openings in body tissue by engaging the adventitia closely adjacent the wall of the body cavity.

There are a wide variety of procedures which require gaining internal access to blood vessels or other body cavities. Many such procedures also require the insertion of treatment devices into the blood vessel or body cavity. Many of these procedures utilize accessible arteries as entry points for the treatment devices. For example, some such arteries include the femoral artery or subclavian artery. There are also a wide variety of procedures which gain access to other body cavities in a minimally invasive fashion.

One problem which must be addressed during these procedures is how to seal or close the opening in the blood vessel or other body cavity once the treatment procedure has been completed. Some prior techniques include simply applying pressure to the opening until it seals itself sufficiently that the pressure may be released. However, this technique often requires that pressure must be consistently applied for an undesirable amount of time after the procedure. Similarly, this type of technique can require a patient's hospitalization to be extended until the treating physician is certain that the closure is complete.

Other techniques have involved suturing the wall of the vessel or body cavity itself. This has typically required the physician to peel back a rather large portion of the tissue surrounding the puncture in order to gain sufficient access to the blood vessel or body cavity that it may be sutured adequately. This can be an undesirably time consuming procedure, and it can result in significant discomfort to the patient.

Still other techniques have involved the insertion of embolic materials adjacent the puncture. Of course, this carries with it its own difficulties. For instances, it is desirable that the embolic material not be placed within a blood vessel or body cavity because this can result in an embolus forming within the blood vessel or body cavity. Similarly, however, it is desirable that the embolic material not be located to far proximal of the puncture because this can result in the blood vessel or body cavity bleeding into the interstitial space proximal of the opening in the blood vessel or body cavity, but distal to the embolic material.

Similarly, when entry is gained into the lumen of the blood vessel by puncturing the blood vessel, the vessel may not have been punctured in a direction entirely orthogonal to the longitudinal axis of the blood vessel. Instead, the blood vessel may be punctured in a "side stick" fashion in which case the puncture is made in an off-center position. In such punctures, it is difficult to locate the outer wall of the blood vessel as well.

SUMMARY OF THE INVENTION

A closure device closes an opening in a body cavity. The closure device includes a closure member that has an external, tissue-engaging surface formed with tissue engaging surface irregularities. An elongate member is disconnectably connected to the closure member.

DETAILED DESCRIPTION OF THE ILLUSTRATIVE EMBODIMENTS

Figure 1:
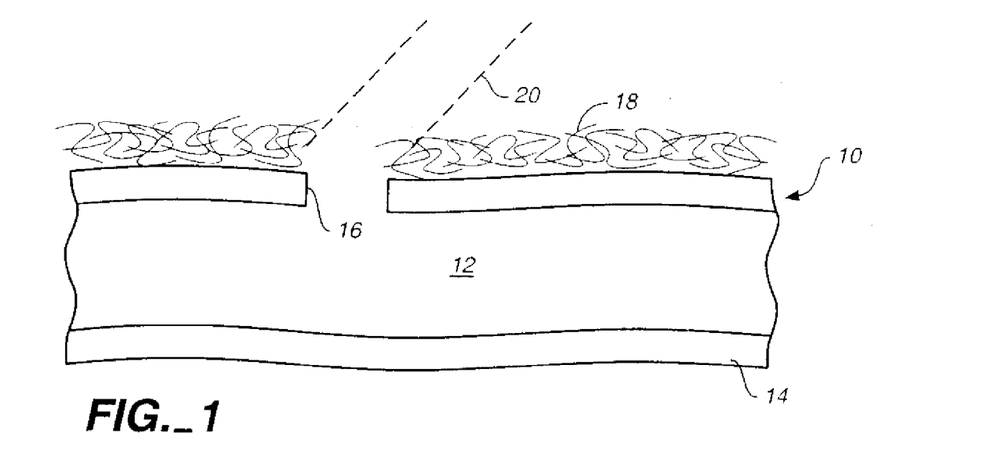
FIG. 1 is a side view of a portion of a blood vessel with an opening therein.

FIG. 1 is a side view of a portion of a blood vessel 10. While the present invention can be used with substantially any body cavity, a blood vessel is described herein for exemplary purposes only. Blood vessel 10 has a lumen 12 defined by a blood vessel wall 14. Blood vessel wall 14 is shown as having an opening 16 therein. Opening 16 can be an opening which was made, for example, in order to perform a treatment procedure during which access to lumen 12 is needed. FIG. 1 also illustrates an access tract or opening 20 which was made when opening 16 was made in vessel 10.

Vessel wall 14 is formed of media having an endothelium inner layer. The media is generally smooth muscular tissue. As is known, the media is surrounded by adventitia 18 which includes fibrous collagen.

Figure 1A:
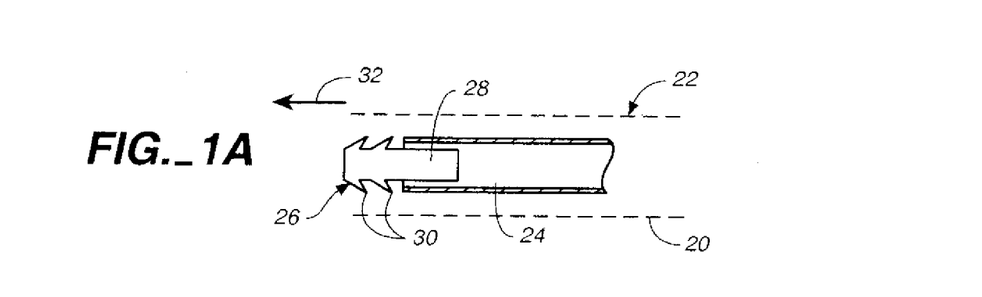

FIG. 1A illustrates a closure apparatus in accordance with one embodiment of the present invention. FIG. 1A shows that closure apparatus 22 includes an elongate delivery member 24 and a closure plug 26. Elongate member 24 is, illustratively, a catheter or wire having a hollow distal tip. Closure plug 26 is made of a plugging material, such as collagen, or another suitable material, which has a proximal end 28 and distal surface irregularities (or hooks) 30. Hooks 30 illustratively comprise annular rings or discrete hooks disposed about the exterior surface of closure plug 26. The hooks 30 can form a regular pattern or be randomly located. Hooks 30 are illustratively oriented such that they are atraumatic when traveling in one direction, such as the direction indicated by arrow 32, and such that they grasp or grip surfaces which they engage when traveling in the opposite direction. In one embodiment, the hooks 30 face proximally so they only grip when traveling proximally. In another embodiment, hooks 30 are oriented randomly and are covered or encapsulated when traveling distally and are exposed when in a desired position or when moved proximally, so they only grip when traveling proximally.

The proximal end 28 of plug 26 is illustratively disconnectably connected to the distal end of elongate member 24. In one illustrative embodiment, proximal end 28 of plug 26 is frictionally engaged within the distal hollow opening in elongate member 24. In another embodiment, plug 26 is attached through a disconnectable adhesive to the distal end of elongate member 24. In yet another embodiment, an active actuation mechanism can be used to disconnect plug 26 from elongate member 24, or a frangible or other disconnectable connection can be used.

Plug 26 is illustratively formed of collagen or any other suitable plugging, biocompatible or bioabsorable material. Similarly, it may require rigidity, in some embodiments, during deployment. Therefore, if it is formed of collagen, it can illustratively be coated, using any suitable coating technique, by a coating which imparts rigidity for an initial 30-90 seconds, or so. However, after that time, the rigidity will illustratively give way to allow fluid to swell plug 26. One such coating may be, for example, hydroxypycelluouse, which is a water soluble polymer with favorable biocompatabiltiy properties.

Figure 2A:
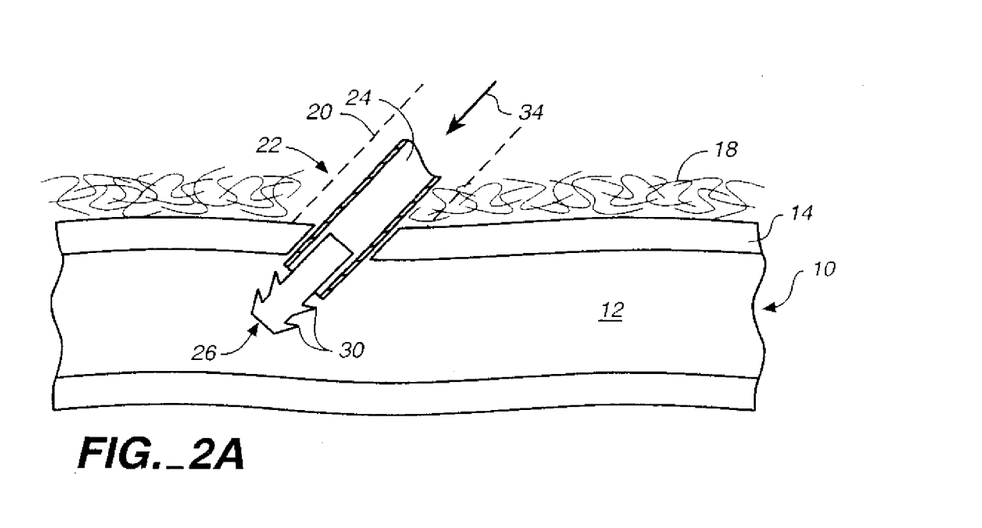
FIGS. 2A-2C illustrate one embodiment of closing the opening in the vessel shown in FIG. 1.
Figure 2B:
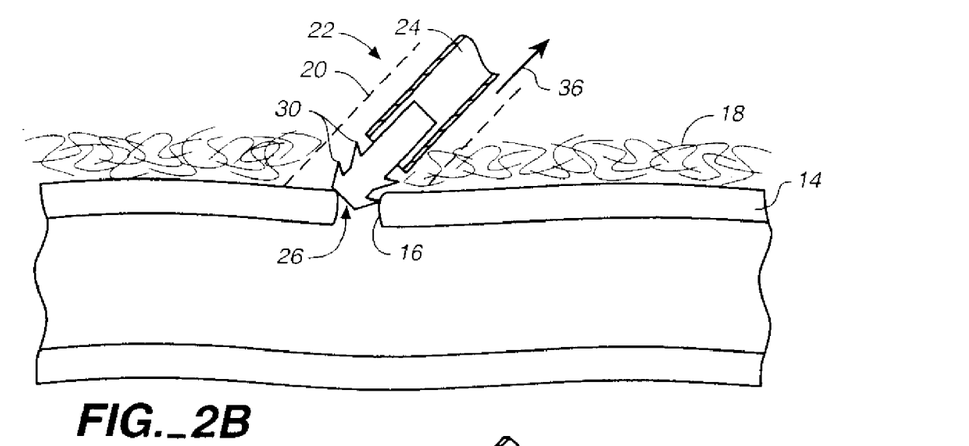
Figure 2C:
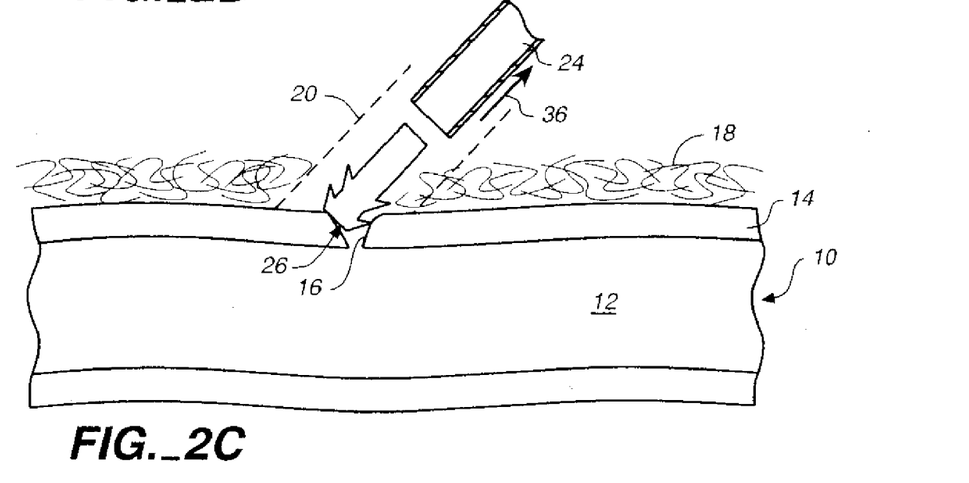

FIGS. 2A-2C illustrate the use of closure plug 26 in closing opening 16 in vessel 10. As shown in FIG. 2A, closure apparatus 22 is first inserted, in a distal direction shown by arrow 34, through access tract 20. Because hooks or ridges 30 are atraumatic when traveling in the distal direction shown by arrow 34, plug 26 and elongate member 24 slide easily through tract 20. Once inside the lumen 12 of vessel 10, elongate member 24 is retracted in the proximal direction opposite that of arrow 34. This is better illustrated in FIG. 2B.

FIG. 2B shows that hooks 30, when retracted in the proximal direction shown by arrow 36, do not engage the relatively smooth media which forms wall 14 of vessel 10. However, when hooks 30 encounter adventitia 18, they immediately become securely lodged in tract 20. In the embodiment shown, the hooks 30 become snagged and entangled in adventitia 18. However, other means of becoming securely lodged are contemplated as well, such as frictionally engagement of the surface irregularity and not simply entanglement. Because adventitia 18 lies immediately proximal of media 14, plug 26 becomes entangled, in place, immediately proximal of opening 16. This placement is highly desired.

FIG. 2C illustrates that elongate member 24 is further withdrawn in the proximal direction shown by arrow 36. However, because the hooks 30 of plug 26 have become securely entangled in the strong fibrous collagen in adventitia 18, the frictional engagement (or other disconnectable engagement) between plug 26 and the distal end of elongate member 24 comes loose, such that plug 26 is disengaged from elongate member 24. This leaves plug 26 in place, where it became entangled, just proximal of opening 16 in media 14 of vessel 10. Elongate member 24 is then simply withdrawn through tract 20.

Figure 3:
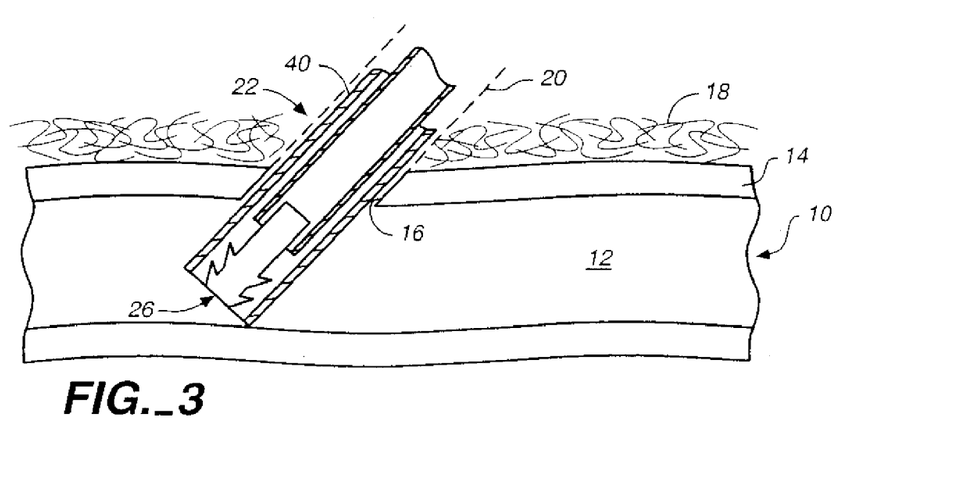
FIG. 3 illustrates another embodiment for delivering a closure device.

FIG. 3 illustrates another embodiment for deploying plug 26. Instead of simply advancing elongate member 24 and plug 26 through tract 20, as shown in FIG. 2A, elongate member 24 and plug 26 are advanced distally into lumen 12 of vessel 10 through an introducer sheath, such as sheath 40. Sheath 40 may be a sheath specially formed to be used with apparatus 22, or it can simply be the introducer sheath which was used in performing the treatment which required the formation of access tract 20. In any case, once plug 26 is in place within lumen 12, introducer sheath 40 is withdrawn proximally and the operation is completed as shown with respect to FIGS. 2B-2C.

Figure 4A:
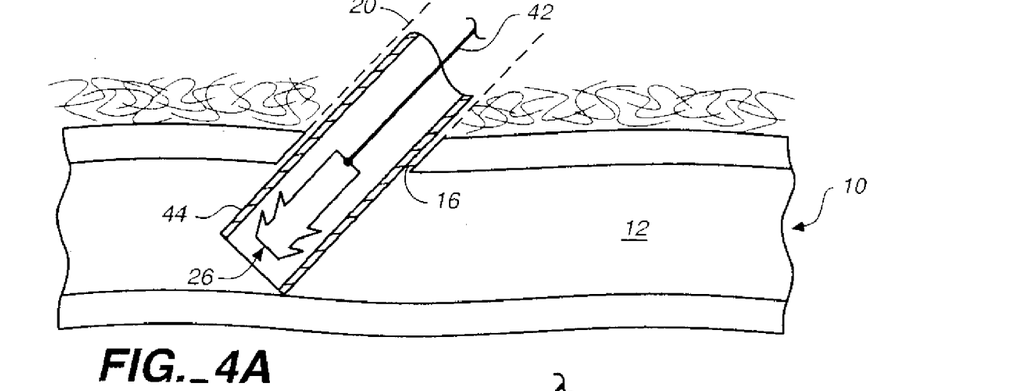
FIGS. 4A-4C illustrate another embodiment for closing the opening shown in FIG. 1.
Figure 4B:
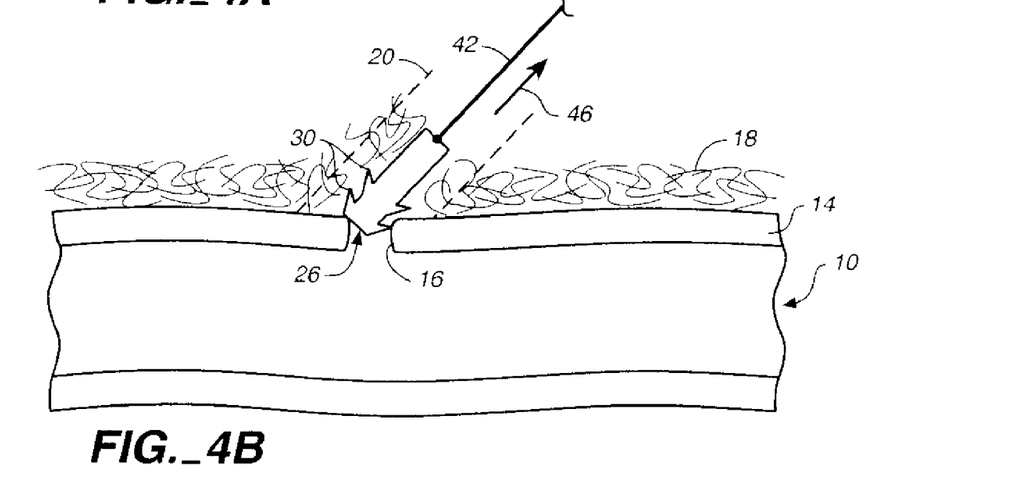
Figure 4C:
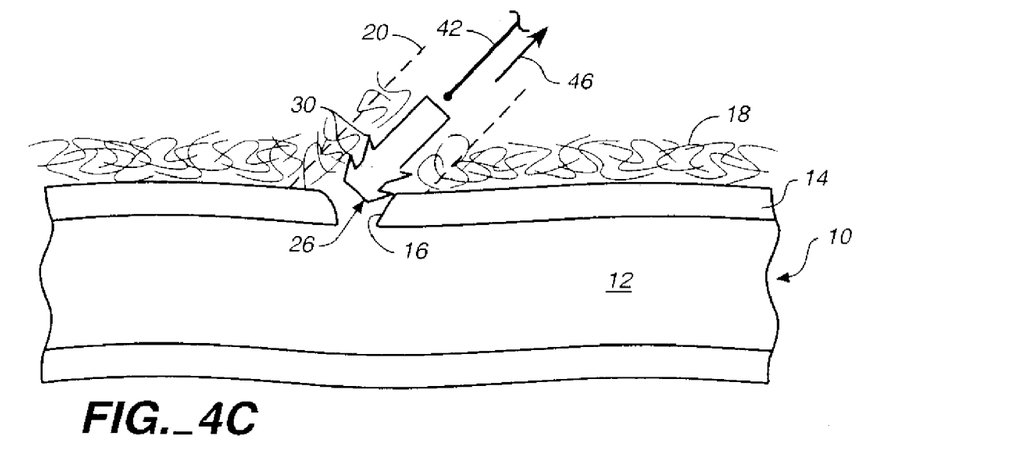

FIGS. 4A-4C illustrate yet another embodiment in which plug 26 is used to close opening 16 in vessel 10. In the embodiment shown in FIGS. 4A-4C, instead of elongate member 24 being used to deploy plug 26, a core wire or other flexible wire or thread 42 is used. In this embodiment, plug 26 is advanced to within lumen 12 of vessel 10 through a delivery catheter (or through an introducer) designated as item 44 in FIG. 4A or it is advanced using a separate pusher, such as a catheter, not shown. In any case, once plug 26 is inserted within lumen 12 of vessel 10, the items used for delivering it, other than elongate wire 42, are withdrawn proximally.

FIG. 4B shows that wire 42 is then withdrawn proximally in the direction indicated by arrow 46. This causes proximal movement of plug 26, through the opening 16 defined by media 14. This also causes hooks or ridges 30 to engage adventitia 18 and become entangled therein.

In one embodiment, wire 42 is connected to the distal end of plug 26 by a frangible connection which can simply be broken when enough force is applied to the connection point. Therefore, as shown in FIG. 4C, once plug 26 becomes entangled in adventitia 14, and proximally directed force is applied to wire 42, the connection point between the proximal end of plug 26 and wire 42 is broken, leaving plug 26 in place. Again, plug 26 is placed just proximal of the media 14 which defines opening 16 in vessel 10. Wire 42 is then simply withdrawn proximally through tract 20.

Figure 5:
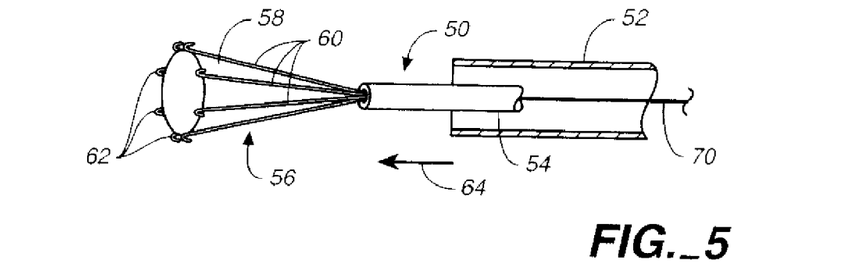
FIG. 5 illustrates another embodiment of a closure device.

FIG. 5 illustrates another embodiment of a closure apparatus 50 in accordance with one embodiment of the present invention. Apparatus 50 includes a delivery sheath 52, a closure sheath 54, and a wire array 56 which is disposed on a cone shaped seal member 58. Elongate members 52 and 54 illustratively extend proximally all the way to a proximal region accessible by a user. Wire array 56 includes a plurality of individual wires 60, each of which have a hook 62 on its distal end. The wires 60 in wire array 56 extend proximally in either a wire bundle 70, or they are connected to a single wire 70 which extends proximally. Hooks 62, like hooks or ridges 30 shown in the above Figures, are oriented such that, as they are advanced in the direction shown by arrow 64, they are atraumatic. However, when withdrawn in the opposite direction, they hook or snag some tissues. Hooks 62 can be formed of conventional hooks used with hook and loop fabric (one embodiment which is sold under the trade name VELCRO), or they can be other desired hooks as well.

FIGS. 6A-6F illustrate one embodiment in which apparatus 50 is used for closing opening 60 in vessel 10.

Figure 6A:
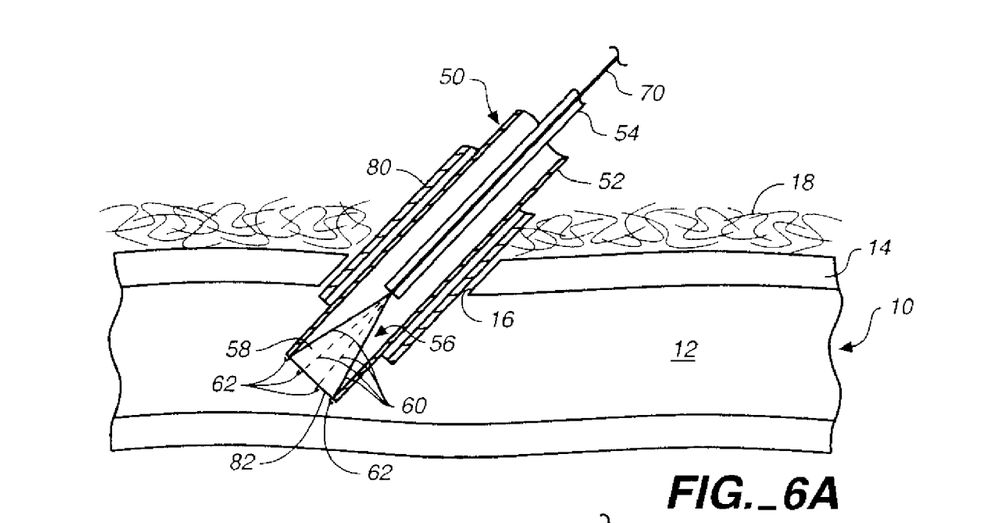
FIGS. 6A-6F illustrate the operation of the closure device shown in FIG. 5.

FIG. 6A shows vessel 10 with an introducer sheath 80 inserted through opening 16 in vessel 10. FIG. 6A also shows that delivery sheath 52 has been advanced distally relative to wire array 56 such that the distal end 82 of delivery sheath 52 is in engagement with hooks 62. In this position, delivery sheath 52 is advanced distally relative to introducer sheath 80 until the distal tip of apparatus 50 is within lumen 12 of vessel 10 as shown in FIG. 6A.

Figure 6B:
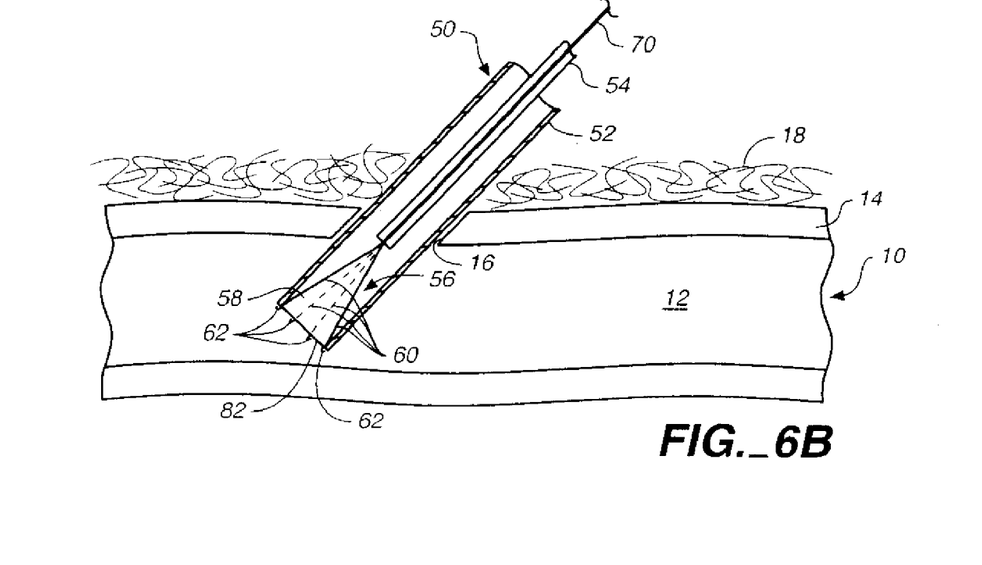

FIG. 6B shows apparatus 50 in the same position as that shown in FIG. 6A, except that introducer sheath 80 has been withdrawn proximally. It can be seen that the sides of opening 16, once introducer sheath 80 is withdrawn, close in around delivery sheath 52.

Figure 6C:
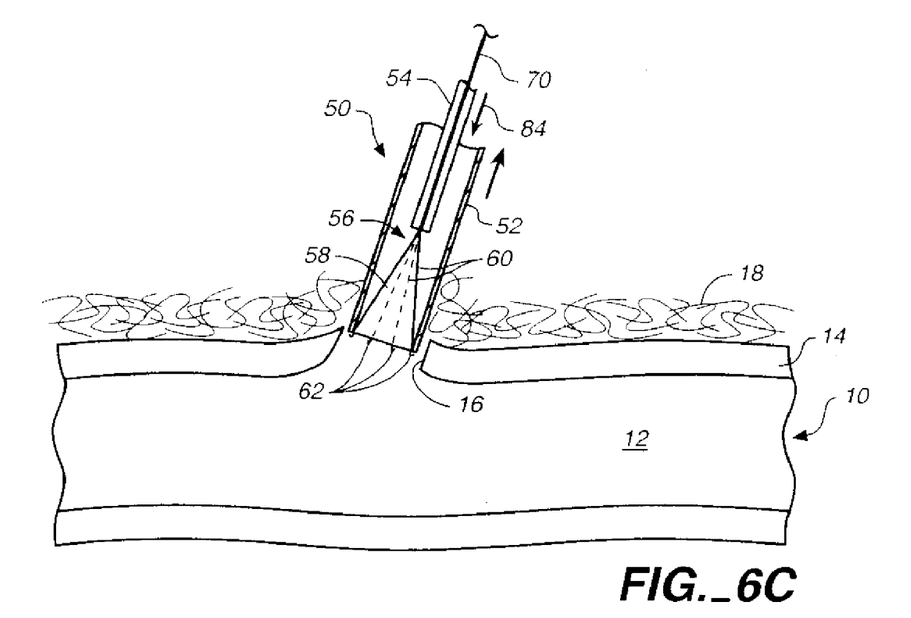

FIG. 6C shows that, in a next step, apparatus 50 is withdrawn proximally. In one embodiment, wire 70 is simply withdrawn proximally. This causes hooks 62 to withdraw delivery sheath 52 and elongate member 54 in the proximal direction as well. Hooks 62 readily pass through the generally smooth media tissue forming opening 16. However, once they encounter adventitia 18, they become firmly entangled therein, as shown in FIG. 6C. The treating physician can easily tell that apparatus 50 is in this position because the resistance to further proximal movement of wire 70 becomes significant.

Figure 6D:
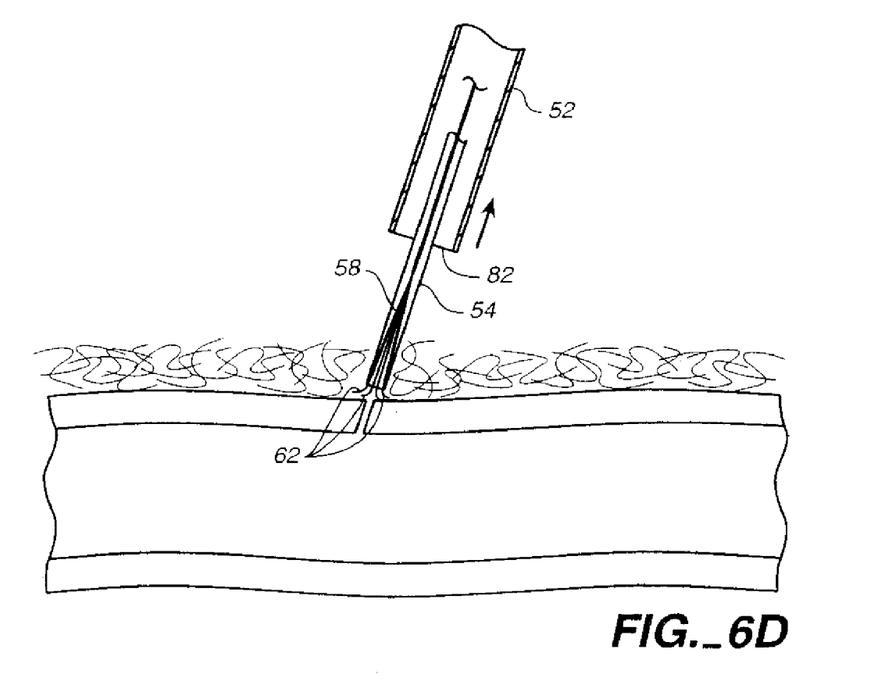

Closure sheath 54 is than advanced proximally over wire 70, wire array 56, and wires 60, in the direction shown by arrow 84. This causes flexible cone-shape seal 58, and wires 60, to collapse inwardly pulling hooks 62 together. FIG. 6D shows closure sheath 54 advanced all the way proximally relative to wire 70, such that hooks 62 are pulled closely adjacent to one another at the distal end of closure sheath 54. Seal 58 is shown collapsed within closure sheath 52.

In one embodiment, the proximal end of closure sheath 54 is illustratively provided with a snap lock fitting. Therefore, when closure sheath 54 is advanced a sufficient distance distally such that hooks 62 are substantially closed and in the position shown in FIG. 6D, the snap lock engages so the user can readily tell this. Of course, any other relative measurement device can be used to indicate that the sheath 54 is in the position shown in FIG. 6D as well.

Figure 6E:
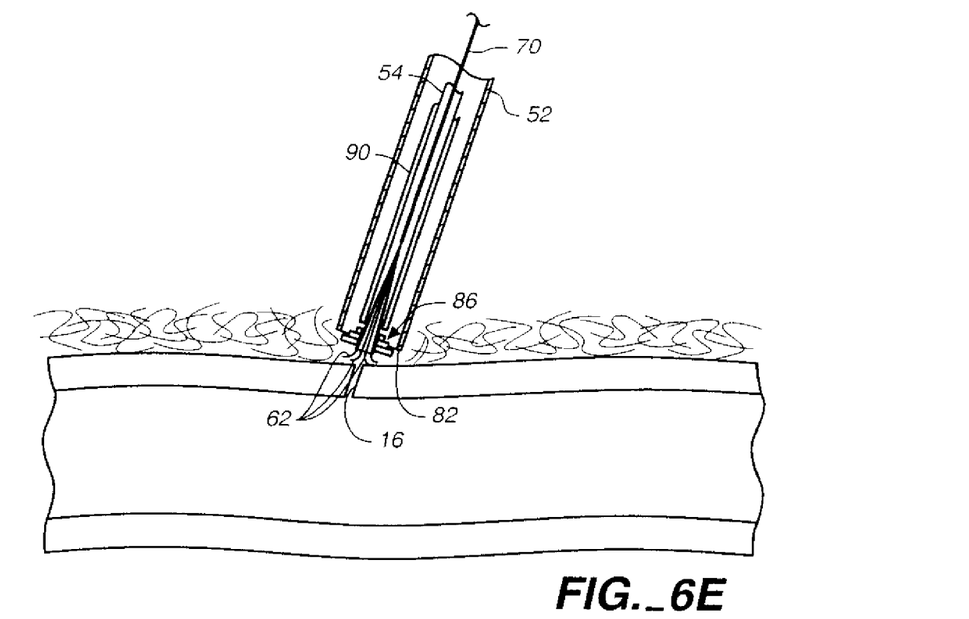
Figure 7:
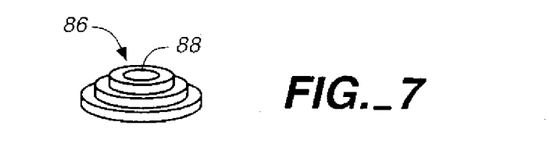
FIG. 7 illustrates a closure plug in accordance with one embodiment of the present invention.

FIG. 6E shows that a plurality of closure plugs 86 have been delivered to the closure site. One embodiment of a plurality of generally disc shaped closure plugs 86 is shown in FIG. 7. The disc shaped plugs 86 are illustratively, arranged generally coaxially and have a central lumen 88 defined therethrough. The plugs can be formed of collagen, absorbable gel, or any other material or substance suitable for closing opening 16. FIG. 6E shows that plugs 86 are illustratively mounted over closure sheath 54 and advanced distally thereover by advancing a second delivery sheath 90. Sheath 90 has a distal end which is sized to engage the most proximal of disc-shaped plugs 86. The disc-shaped plugs 86 are advanced through delivery sheath 52 by advancing delivery sheath 90 over closure sheath 54. Plugs 86 are advanced to the position shown in FIG. 6E, just proximal of opening 16.

Figure 6F:
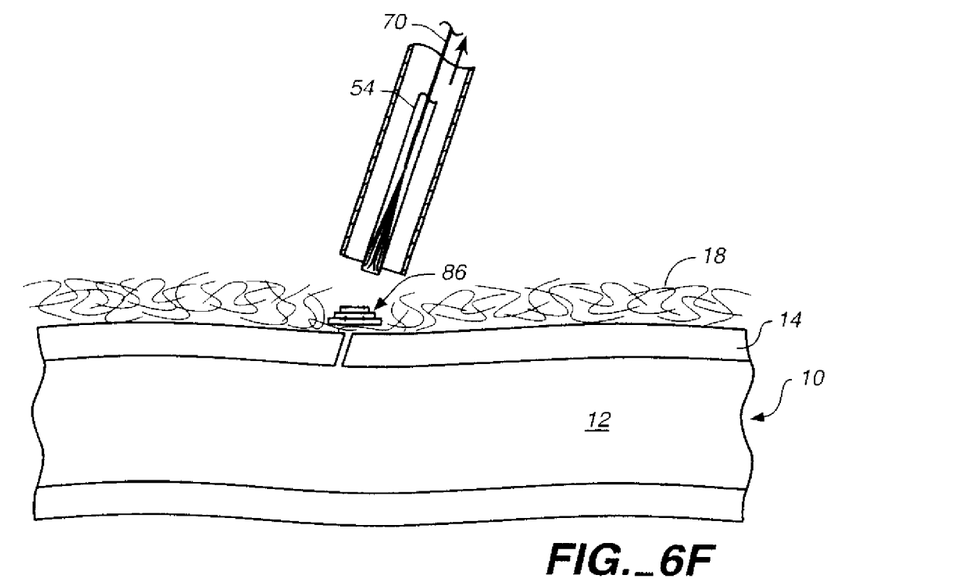

Next, wire array 56 is removed. This is better illustrated with respect to FIG. 6F. FIG. 6F shows that closure sheath 54 is advanced further distally until it deforms hooks 62 until they reside within the distal end of closure sheath 54. Once in that position, wires 70 and closure sheath 54 are withdrawn proximally, to the position shown in FIG. 6F relative to second delivery sheath 90. At anytime during this process, and after delivery of plugs 86, the first delivery sheath 52 can be withdrawn proximally.

Delivery sheath 90 can then be used to tamp plugs 86 firmly in place. Then, the entire system is withdrawn proximally, in any desired order.

Figures 8A, 8B, 8C, 9A:
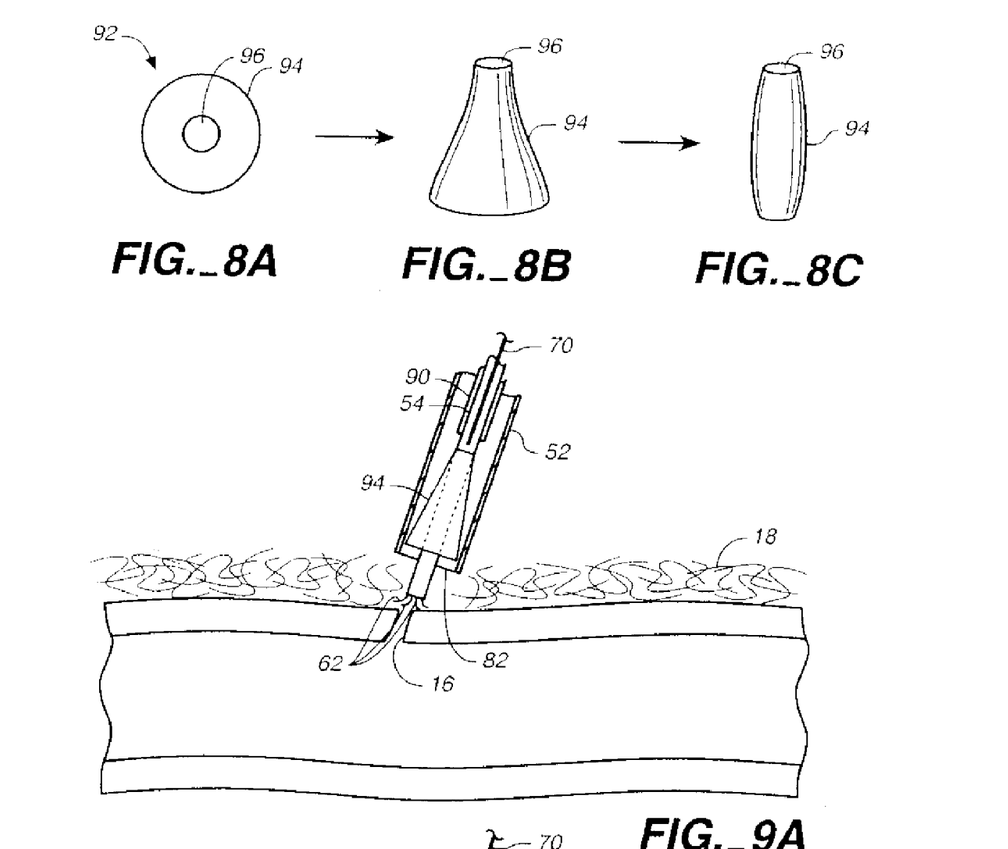
FIGS. 8A-8C illustrate the formation of another closure plug in accordance with one embodiment of the present invention.
FIGS. 9A and 9B illustrate a closure operation using the closure plug shown in FIGS. 8A-8C.

FIGS. 8A-8C illustrate another embodiment of a plug 92 which can be formed and used in accordance with the system shown in FIGS. 6A-6F. Plug 92 is formed of a sheet of material 94 having a generally centrally located aperture 96 therein. Sheet 94 can be substantially any shape, but is shown in a generally circular shape for the sake of simplicity. Sheet 94 is illustratively formed of a vascular occluding material such as that in the QuickSeal Arterial Closure System from Sub-Q, Inc. of San Clamente, Calif. Sheets 94 are illustratively pliable material which can be bent and folded. Therefore, sheets 94 are folded or twisted to a fully collapsed shape having a generally central lumen extending therethrough, as shown in FIGS. 8B and 8C. Instead of loading disc-shaped plugs 86 over closure sheath 54, plugs 94 are loaded thereover.

Figure 9B:
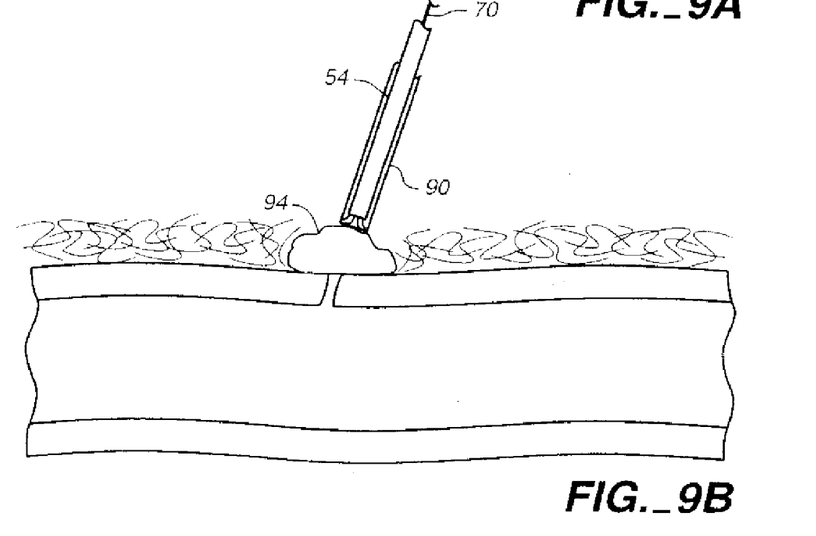

FIGS. 9A and 9B illustrate delivery of a plug 94 using the apparatus shown in FIGS. 6A-6F. Plug 94 is advanced over closure sheath 54 using sheath 90. Delivery sheath 52 is then withdrawn proximally, and closure sheath 54 is advanced distally to retrieve hooks 62. Then, closure sheath 54 is withdrawn proximally and sheath 90 is advanced distally to tamp in place plug 94. This is shown in FIG. 9B. Of course, a plurality of plugs 94 can be loaded onto closure sheath 54 and delivered by sheath 90, either one at a time, or multiple plugs at a single time, as desired.

Figure 10A:
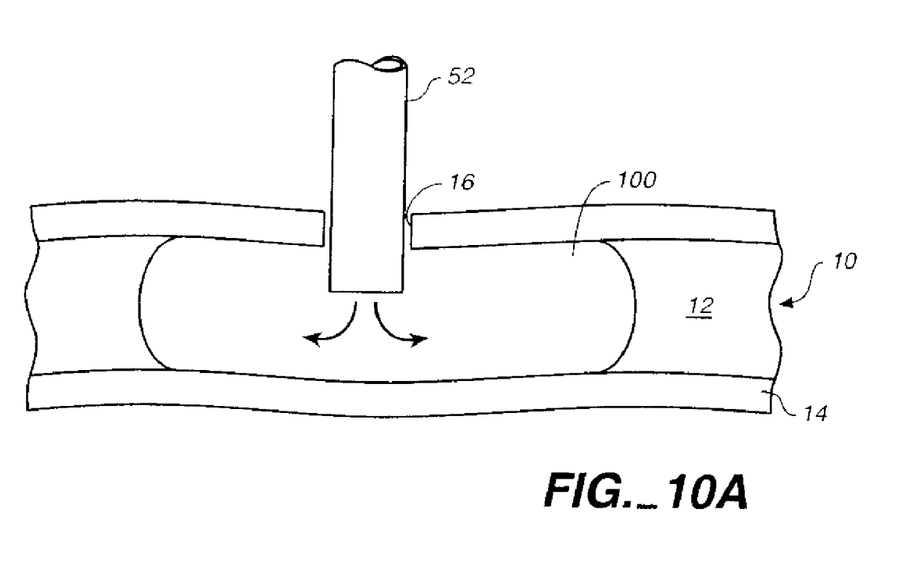
FIGS. 10A-10D illustrate a closure device in accordance with another embodiment of the present invention.

FIGS. 10A-10D illustrate another embodiment of a closure device in accordance with the present invention. In FIG. 10A, delivery sheath 52 is shown inserted within the lumen 12 of vessel 10. A small bolus of inert gas, such as $CO_2$, is then injected into vessel 10 through sheath 52 (which can be attached to a source of the inert gas). This forms a dry field 100 of the inert gas within the lumen 12 of vessel 10. Distal pressure on vessel 10 may be used in order to better hold the gas bolus 100 in place.

Figure 10B:
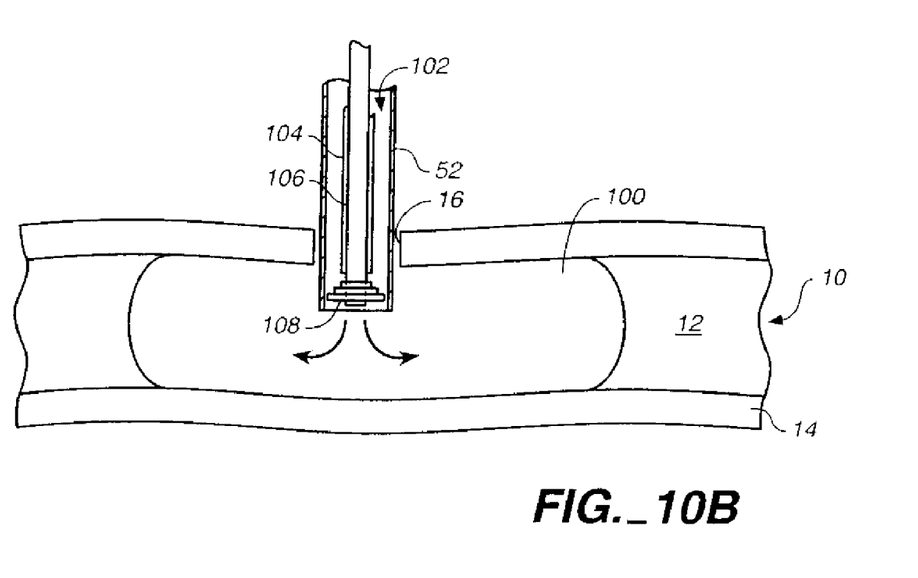

FIG. 10B shows that a delivery apparatus 102 is then inserted through sheath 52 into lumen 12 of vessel 10. Delivery apparatus 102 includes an elongate delivery sheath 104 an elongate delivery member 106, and liquid swellable plug or plugs 108. Plugs 108 are inserted through sheath 52 until swellable plugs 108 are within the lumen 12 and reside at the distal end of sheath 52. This can be ensured by proximal markings on sheaths 52 and 104, or using any other desired mechanism or method. Because swellable plugs 108 are within a dry field formed by bolus 100, they do not begin to swell or to occlude.

Figure 10C:
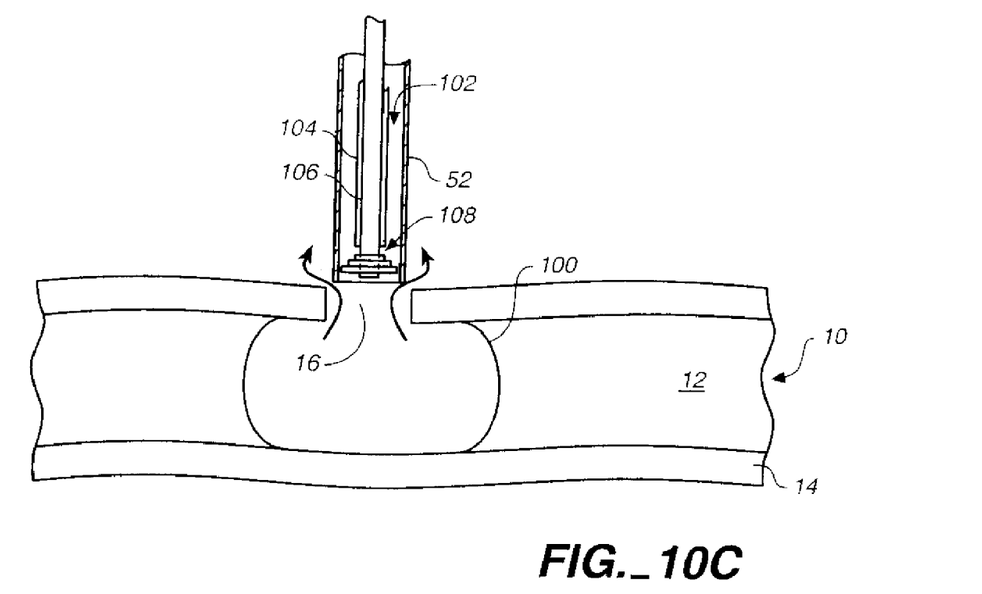
Figure 10D:
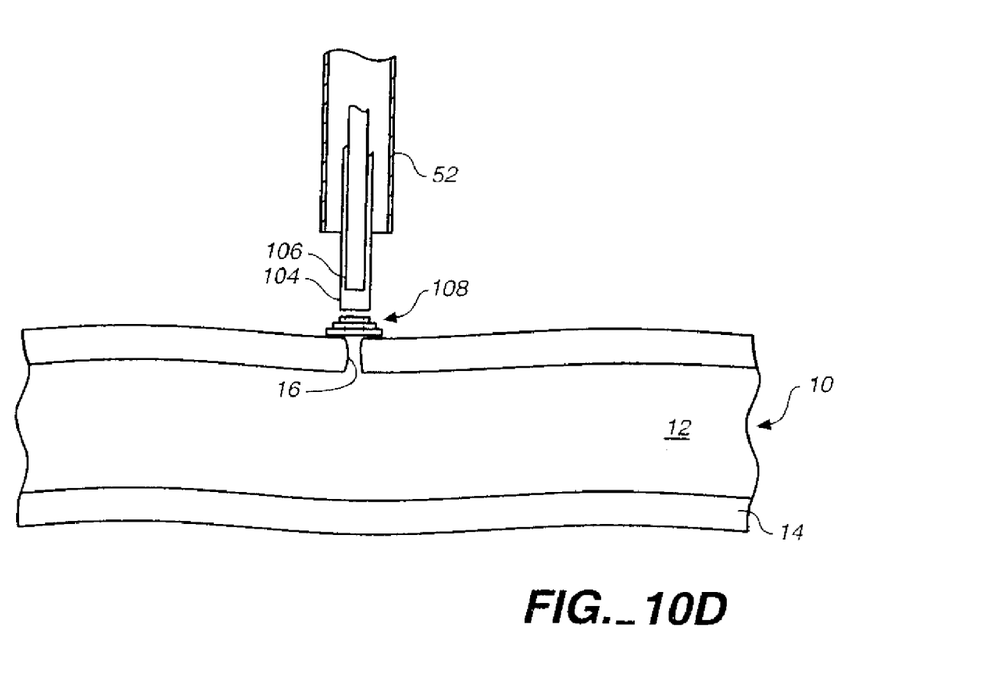

FIG. 10C shows that sheath 52, along with swellable plugs 108, are then withdrawn proximally. As soon as sheath 52 and plugs 108 are withdrawn proximally to a point outside of vessel 10, the gas bolus 100 escapes from vessel 10. This produces a visual and audio feedback indicating that sheath 52 and plugs 108 have just cleared vessel 10. Sheath 52 is then withdrawn further proximally. Once the gas bolus 100 has vented, blood from within vessel 10 engages and wets swellable plugs 108. Sheaths 52 and 104 and delivery member (or wire) 106, are then withdrawn proximally as shown by FIG. 10B, leaving plugs 108 in place in the desired position.

Although the present invention has been described with reference to preferred embodiments, workers skilled in the art will recognize that changes may be made in form and detail without departing from the spirit and scope of the invention.

What is claimed is:

1. A closure apparatus for closing an opening in a body cavity, a smooth media layer being located proximal to the opening and a fibrous tissue layer being located proximal to the smooth media layer, the closure apparatus comprising:
    a plurality of fibrous tissue engaging members coupled to a proximally extending elongate member, the fibrous tissue engaging members being movable between an expanded position and a collapsed position;
    a closure sheath sized to receive the elongate member and slidable thereover to move the fibrous tissue engaging members from the expanded position to the collapsed position;
    a delivery sheath sized to receive the closure sheath and having a distal end sized to engage the fibrous tissue engaging members when in the expanded position; and
    a closure member having an aperture defined therein sized to receive the closure sheath.

2. The closure apparatus of claim 1, wherein the closure member comprises:
    a generally disc-shaped member having the aperture defined therein.

3. The closure apparatus of claim 2, wherein the generally disc-shaped closure member comprises:
    a plurality of disc-shaped pieces each having an aperture defined therein and being arranged in a generally coaxial orientation.

4. The closure apparatus of claim 1, wherein the closure member comprises:

a sheet of pliable, swellable material folded into a generally tubular shape having the aperture defined therethrough.

5. The closure apparatus of claim 1, wherein the closure member comprises:
a plurality of sheets of pliable, swellable material, each folded into a generally tubular shape having the aperture defined therethrough.

6. The closure apparatus of claim 5, wherein the plurality of sheets are disposed over the closure sheath in a generally coaxial arrangement.

7. The closure apparatus of claim 1, wherein the fibrous tissue engaging members comprise:
a plurality of hook-shaped members.

8. The closure apparatus of claim 7, wherein the plurality of hook-shaped members are oriented to be proximally facing hook-shaped members.

9. The closure apparatus of claim 8, wherein the proximally facing hook-shaped members are sufficiently resilient to deform to be received within the closure sheath upon distal advancement of the closure sheath distally beyond the proximally facing hook-shaped members.

10. The closure apparatus of claim 1, wherein the delivery sheath is in engagement with the plurality of fibrous tissue engaging members in the expanded position as the plurality of fibrous tissue engaging members is advanced distally into the body cavity opening.

11. The closure apparatus of claim 10, wherein the plurality of fibrous tissue engaging members is configured to pass through the smooth media layer and become entangled with the fibrous tissue layer when moved proximally away from the body cavity opening.

* * * * *